US007470813B2

(12) United States Patent
Gloegaard et al.

(10) Patent No.: US 7,470,813 B2
(45) Date of Patent: Dec. 30, 2008

(54) METHOD FOR THE PRODUCTION OF PYRUVIC ACID

(75) Inventors: Christian Gloegaard, Oslo (NO); Tom Christian Berg, Oslo (NO)

(73) Assignee: GE Healthcare Limited, Amersham (GB)

( * ) Notice: Subject to any disclaimer, the term of this patent is extended or adjusted under 35 U.S.C. 154(b) by 0 days.

(21) Appl. No.: 12/056,582

(22) Filed: Mar. 27, 2008

(65) Prior Publication Data

US 2008/0242889 A1     Oct. 2, 2008

(30) Foreign Application Priority Data

Mar. 30, 2007   (NO)   ................................. 20071682

(51) Int. Cl.
*C07C 59/00*     (2006.01)
(52) U.S. Cl. ..................................... 562/577
(58) Field of Classification Search ........................ None
See application file for complete search history.

(56) References Cited

U.S. PATENT DOCUMENTS 4,247,716 A     1/1981   Kiyoura

FOREIGN PATENT DOCUMENTS

| EP | 337246 | 7/1992 |
|----|--------|--------|
| EP | 313850 | 1/1993 |
| JP | 8183753 | 7/1996 |
| WO | 95/00656 | 1/1995 |
| WO | 2006/011809 | 2/2006 |
| WO | 2006/011810 | 2/2006 |
| WO | 2006/054903 | 2/2006 |
| WO | 2007/069909 | 6/2007 |
| WO | 2007/111515 | 10/2007 |

OTHER PUBLICATIONS

R.W. Friesen, J. Chem. Soc., Perkin Trans. 1, 2001, 1969-2001.*
Friesen, Richard, "Generation and reactivity of alpha-metalated vinyl ethers" J. Chem. Soc., Perkin Trans. 1, 2001, pp. 1969-2001.
Verkruujsse, H.D., et al. "Convenient procedures for the alpha-metallation of vinylic ethers and thioethers" J. Organomet. Chem, 1987, 332, pp. 99-103.
Sheng, S, et.al. "Polymer-supported beta-bromoethyl selenide: an efficient reagent for the synthesis of aryl vinyl ethers" Synthesis 2004, No. 17, pp. 2833-2836.
Bosch, M. et.al., "Synthesis of Allyl and Alkyl vinyl ethers using an in situ prepared air-stable palladium catalyst. Efficient transfer vinylation of primary secondary and tertiary alcohols" J. Org. Chem., 2003, 68, pp. 5225-5227.
Taylor, R. "The mechanism of thermal eliminations. Part 26. Substituent effects at each carbon of vinyl ethers: non-planarity of the transition state" J. Chem. Soc., Perkin Trans. 1988 pp. 737-743.
Grobelny, et.al. "Electron-transfer reduction of selected alcohols with alkalide K–, K+(15-crown-5)2 via organometallic intermediates" J. of Organometallic Chemistry, 689, 2004 pp. 2361-2367.
Seebach, D. et.al., "Generation and synthetic applications of 2-lithio-1,3-dithianes" J. Org. Chem., vol. 40, No. 2, 1975 pp. 231-237.
Anker, H.S. "Synthesis of carbonyl-labeled pyruvic acid" J. Biol. Chem, 176 (1948, pp. 1333-1335.
Shimano, et.al., Tetrahedron Lett., 1994, 35 p. 7727-7730.

* cited by examiner

*Primary Examiner*—Karl J Puttlitz
(74) *Attorney, Agent, or Firm*—Craig Bohlken

(57) ABSTRACT

The invention relates to a method for the production of pyruvic acid, in particular pyruvic acid that is $^{13}$C-enriched at the C1-atom, i.e. $^{13}C_1$-pyruvic acid.

15 Claims, No Drawings

METHOD FOR THE PRODUCTION OF PYRUVIC ACID

FIELD OF THE INVENTION

The invention relates to a method for the production of pyruvic acid, in particular pyruvic acid that is $^{13}$C-enriched at the C1-atom, i.e. $^{13}$C$_1$-pyruvic acid.

BACKGROUND OF THE INVENTION

Pyruvate, i.e. a salt of pyruvic acid, is an important intermediate in the pathway of carbohydrate metabolism and fatty acid metabolism in the human and animal body. In order to gain insight in these metabolic pathways, $^{13}$C-isotopically enriched pyruvate (hereinafter $^{13}$C-pyruvate) has been used to detect metabolites of pyruvate generated in the living body by $^{13}$C-NMR.

Further, hyperpolarised $^{13}$C-pyruvate has been used as imaging agent in $^{13}$C-magnetic resonance (MR) imaging (MRI) and/or spectroscopy (MRS) for in vivo and in vitro $^{13}$C-MR studies of metabolic processes in the human and animal body.

The term "hyperpolarised" denotes an enhanced nuclear polarisation of the $^{13}$C-nuclei present in the pyruvate molecule. Upon enhancing the nuclear polarisation of the $^{13}$C-nuclei, the population difference between excited and ground nuclear spin states of these nuclei is significantly increased and thereby the MR signal intensity is amplified by a factor of hundred and more. When using hyperpolarised $^{13}$C-pyruvate, as MR imaging agent, there will be essentially no interference from background signals as the natural abundance of $^{13}$C is negligible. Thus the image contrast will be advantageously high. Hyperpolarised $^{13}$C-pyruvate may for instance be used as an MR imaging agent for in vivo tumour imaging as described in detail in WO-A-2006/011810 and WO-A-2006/011809. Further, it may be used for assessing the viability of myocardial tissue by MR imaging as described in detail in WO-A-2006/054903. Hyperpolarised $^{13}$C-pyruvate can be obtained by for instance dynamic nuclear polarisation (DNP). In this method, $^{13}$C-pyruvic acid can be hyperpolarised and is subsequently converted to $^{13}$C-pyruvate by using a base for dissolving the solid hyperpolarised $^{13}$C-pyruvic acid obtained by DNP. Alternatively, $^{13}$C-pyruvate can be directly used in the DNP process in form of certain salts. The production of hyperpolarised $^{13}$C-pyruvate is described in detail in WO-A-2006/011809, in WO-A-2007/069909 and WO-A-2007/111515, the latter two applications describing the use of $^{13}$C-pyruvates in the described DNP method.

In the body, pyruvate is converted (metabolised) into different compounds: its transamination results in alanine, via oxidative decarboxylation; pyruvate is converted into acetyl-CoA and carbon dioxide (which is further converted to bicarbonate), the reduction of pyruvate results in lactate and its carboxylation in oxaloacetate.

Hyperpolarised $^{13}$C-pyruvate which is labelled at the C1-atom, i.e. $^{13}$C$_1$-pyruvate is preferably used as MR imaging agent since it has a long T$_1$ relaxation in human full blood (42 s at 37° C.), which allows real-time monitoring and detection of its conversion to hyperpolarised $^{13}$C-lactate, hyperpolarised $^{13}$C-bicarbonate and hyperpolarised $^{13}$C-alanine by $^{13}$C-MR/NMR.

Several methods for the production of pyruvic acid are known in the art which can be grossly divided into methods involving the use of microorganisms or enzymes and chemical synthesis.

An example of an enzyme based method for the production of pyruvic acid is the enzymatic oxidation of lactic acid, as for instance described in WO-A-95/00656. Enzymatic oxidation often results in byproducts as reactive hydrogen peroxide is produced during said enzymatic oxidation. Further, an upscale of enzymatic processes to an industrial process level is often problematic or impossible. Examples for methods involving the use of microorganisms for the production of pyruvic acid are for instance described in EP-A-313 850. A disadvantage of these microbiological production processes is that can be difficult and time consuming to separate, isolate and purify pyruvic acid from the complex reaction mixtures, e.g. form complex fermentation broths.

Examples of chemical synthesis for the production of pyruvic acid are largely based on the oxidation of various starting materials like propylene glycol (as described in EP-A-337 246), hydroxyacetone (as disclosed in U.S. Pat. No. 4,247, 716) or lactic acid (see for instance JP-A-8183753). However, for the production of isotopically enriched $^{13}$C-pyruvic acid, the use of a commercially available isotopically enriched starting material or an isotopically enriched starting material that is obtainable by a straightforward chemical synthesis is greatly preferred.

Further, to be used as hyperpolarised MR imaging agent, $^{13}$C$_1$-pyruvic acid has to be of high purity. It is also important that the synthesis can be upscaled since when the compound is used as an MR imaging agent, relatively large amounts of $^{13}$C$_1$-pyruvate need to be injected per dose and hence relatively large amounts of $^{13}$C$_1$-pyruvic acid need to be polarised. Several methods for the chemical synthesis of isotopically enriched pyruvic acid are known in the art. Seebach et al., Journal of Organic Chemistry 40(2), 1975, 231-237 describe a synthetic route that relies on the protection and activation of a carbonyl-containing starting material as an S,S-acetal, e.g. 1,3-dithian or 2-methyl-1,3-dithian. The dithian is metallated and reacted with a methyl-containing compound and/or $^{13}$CO$_2$. By using the appropriate isotopically enriched $^{13}$C-compound as outlined in this reference, it is possible to obtain $^{13}$C$_1$-pyruvate, $^{13}$C$_2$-pyruvate or $^{13}$C$_{1,2}$-pyruvate which may then be converted into the free acid by methods known in the art.

S. H. Anker et al., J. Biol. Chem.176 (1948), 1333-1335 describe a different synthetic route that starts from acetic acid, which is first converted into acetyl bromide and then reacted with Cu$^{13}$CN. The nitrile obtained is converted into pyruvic acid via the amide. However, the use of toxic cyanides limits the application of this method to small scale production of $^{13}$C-labelled pyruvic acid.

We have now surprisingly found a method to produce pyruvic acid and pyruvic acid which is isotopically enriched at the C1-atom, preferably $^{13}$C$_1$-pyruvic acid in excellent purity. The method is easily upscaled such that lager amounts of pyruvic acid or isotopically enriched pyruvic acid can be prepared. Apart from $^{13}$C-enriched pyruvic acid, the method can also be used to produce $^{11}$C-enriched pyruvic acid, $^{11}$C$_1$-pyruvic acid. Such a compound can be used as a tracer in positron emission tomography (PET).

DESCRIPTION OF THE INVENTION

The invention provides a method for producing pyruvic acid by a) reacting a vinyl ether of formula (I)

wherein

R is a straight chain or branched C$_1$-C$_6$-alkyl group or an aliphatic or aromatic ring comprised of 5-7 carbon atoms, optionally substituted with one or more lower alkyl groups, halogen groups or nitro groups
with an alkyllithium base to obtain an α-metalated vinyl ether b) reacting the α-metalated vinyl ether obtained in step a) with $CO_2$ to obtain an α-alkoxy acrylic acid of formula (II)

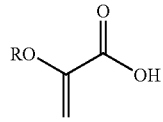

(II)

wherein
R is defined as above; and c) subsequently hydrolysing the α-alkoxy acrylic acid of formula (II).

In a preferred embodiment the method is used for producing isotopically enriched pyruvic acid by using in step b) isotopically enriched $CO_2$. In a more preferred embodiment the method is used for producing $^{13}C_1$-pyruvic acid by using in step b) $^{13}CO_2$ or for producing $^{11}C_1$-pyruvic acid by using in step b) $^{11}CO_2$.

In a preferred embodiment of the method of the invention, R is a straight chain or branched $C_1$-$C_6$-alkyl group, preferably methyl, ethyl, n-propyl, isopropyl, n-butyl, isobutyl, tert-butyl or n-pentyl. In a more preferred embodiment, R is ethyl, n-propyl, isopropyl, n-butyl, isobutyl or tert-butyl. In a most preferred embodiment, R is ethyl.

In another preferred embodiment, R is an aliphatic or aromatic ring comprised of 5-7 carbon atoms, preferably cyclohexyl or phenyl, optionally substituted with one or more lower alkyl groups, preferably $C_1$-$C_3$-alkyl groups, halogen groups or nitro groups. If an R substituted with a lower alkyl group, R may be attached to the oxygen atom in formula (I) and (II) either via the lower alkyl group or via the aliphatic or aromatic ring. As an example R is an aromatic ring comprised of 6 carbon atoms which is substituted with a methyl group. In this embodiment, R may thus be benzyl, i.e. *—$CH_2$-$C_6H_5$ (* denotes the attachment to the oxygen atom in formula (I) and (II)) or methyl phenyl, i.e. *—$C_6H_4$-$CH_3$. In a more preferred embodiment, R is cyclohexyl, 2-phenylethyl, 3-methylphenyl, 4-tert-butylphenyl, 4-bromophenyl or 4-nitrophenyl.

Using a more lipophilic residue R, like for instance a straight chain $C_5$-$C_6$-alkyl group or an aromatic ring can be an advantage since this facilitates the isolation of the α-alkoxy acrylic acid after step b), if such isolation is performed. However, compounds of formula (I) comprising such a lipophilic residue are more costly, if commercially available, or need to be synthesised.

Compounds of formula (I) wherein R is ethyl are most preferred since ethyl vinyl ether is readily commercially available at reasonable costs.

Most of the above-mentioned vinyl ethers are commercially available compounds or can be prepared by synthetic routes described in the literature. The synthesis of vinyl ethers wherein R is 3-methylphenyl, 4-tert-butylphenyl, 4-bromophenyl or 4-nitrophenyl is described in S—R. Sheng et al., Synthesis 2004, 17, 2833-2836. For the synthesis of vinyl ether wherein R is benzyl see M. Bosch et al., J. Org. Chem. 2003, 68, 5225-5227 or Z. Grobelny et al., J. Organomet. Chem. 2004, 689, 2361-2367. The synthesis of vinyl ether wherein R is 2-phenylethyl is described in R. Taylor, J. Chem. Soc. Perkin Trans. II, 1988, 737-743.

If $^{13}C_1$-pyruvic acid is obtained by the method of the invention, said $^{13}C_1$-pyruvic acid may be directly used in the DNP process to produce hyperpolarised $^{13}C_1$-pyruvic acid. A process for the DNP hyperpolarisation of $^{13}C_1$-pyruvic acid is described in WO-A-2006/011809.

Preferred salts are those $^{13}C_1$-pyruvates which comprise an inorganic cation from the group consisting of $NH_4^+$, $K^+$, $Rb^+$, $Cs^+$, $Ca^{2+}$, $Sr^{2+}$ and $Ba^{2+}$, preferably $NH_4^+$, $K^+$, $Rb^+$ or $Cs^+$, more preferably $K^+$, $Rb^+$, $Cs^+$ and most preferably $Cs^+$, as in detail described in WO-A-2007/111515.

Further preferred are salts are $^{13}C_1$-pyruvates of an organic amine or amino compound, preferably TRIS-$^{13}C_1$-pyruvate or meglumine-$^{13}C_1$-pyruvate, as in detail described in WO-A-2007/069909.

If $^{11}C_1$-pyruvic acid is obtained by the method of the invention, said $^{11}C_1$-pyruvic acid can be converted to $^{11}C_1$-pyruvate, e.g. sodium $^{11}C_1$-pyruvate by the use of a base, e.g. neutralization with aqueous NaOH. A process for the neutralization of $^{13}C_1$-pyruvic acid and suitable bases is described in WO-A-2006/011809 and said process can also be used for the neutralization of $^{11}C_1$-pyruvic acid. The $^{11}C_1$-pyruvate can be used as a tracer in PET imaging.

In step a) of the method of the invention, a vinyl ether of formula (I) is reacted with an alkyllithium base to obtain an α-metalated vinyl ether. In a preferred embodiment, the alkyllithium base is a butyllithium (BuLi) base, preferably n-BuLi, sec-BuLi or tert-BuLi, more preferably tert-BuLi.

In a preferred embodiment, one or more additives that increase the reactivity of the alkyllithium base are added to the alkyllithium base used in the method of the invention. In a more preferred embodiment, potassium tert-butoxide (tert-BuOK) is used as an additive and is most preferably added to n-BuLi. The mixture of n-BuLi and tert-BuOK is called "Lochmann-Schlosser base" and said mixture is prepared in situ.

Other additives which increase the reactivity of the alkyllithium base, like tetramethylethylenediamine (TMEDA) or hexamethylphosphoramide (HMPA) are preferably present in the reaction of step a) of the method of the invention. In a preferred embodiment, TMEDA is used as an additive in the reaction of step a).

The reaction of vinyl ethers of formula (I) with alkyllithium bases to obtain α-metalated vinyl ethers is known in the art. For an overview see R. W. Friesen, J. Chem. Soc., Perkin Trans. 1, 2001, 1969-2001. In a preferred embodiment of step a), the vinyl ether of formula (I), preferably ethyl vinyl ether is dissolved in an aprotic polar solvent like tetrahydrofuran (THF) or tetrahydropyran (THP) or mixtures of aprotic polar solvents or in an aprotic non-polar solvent like hexane or pentane. Aprotic polar solvents have been used for reacting ethyl vinyl ether with tert-BuLi. The use of THP circumvented earlier observed deprotonation of THF (M. Shimano et al., Tetrahedron Lett., 1994, 35, 7727). Aprotic non-polar solvents have been used for reacting ethyl vinyl ether with Lochmann-Schlosser base (H. D. Verkruujsse et al., J. Organomet. Chem., 1987, 332, 99.)

The dissolved vinyl ether is cooled to a temperature of below 0° C., preferably of below −20° C. and more preferably of below −60° C. The alkyllithium base and optional additives like tert-BuOK or TMEDA are added and the mixture is stirred. In a preferred embodiment, the dissolved vinyl ether, TMEDA and tert-BuOK are cooled to a temperature of below −60° C. and n-BuLi, preferably dissolved in an aprotic non-polar solvent like hexane or pentane is added drop wise. The Lochmann-Schlosser base is thus generated in situ. The reaction of step a) is preferably carried out under inert atmosphere, for instance under nitrogen or argon atmosphere.

Suitably the ratio of the concentrations of alkyllithium base and vinyl ether used in step a) is about 1 and the use of 0.8-1.5 equivalents of alkyllithium base per equivalent vinyl ether is preferred.

In step b) of the method of the invention, the α-metalated vinyl ether obtained in step a) is reacted with $CO_2$ to an α-alkoxy acrylic acid of formula (II). In a preferred embodiment, the crude reaction mixture from step a) is directly used in step b).

Any type of $CO_2$ may be used in step b), i.e. solid $CO_2$, supercritical "liquid" $CO_2$ or gaseous $CO_2$. To obtain $^{13}C_1$-pyruvic acid by the method of the invention, $^{13}CO_2$, which is a commercially available compound, is used in step b). If the method of the invention is carried out on a small scale, solid $CO_2$ may be used. However, for large scale synthesis of pyruvic acid and/or the synthesis of $^{13}C_1$-pyruvic acid it is preferred to use gaseous $CO_2$ or supercritical $CO_2$, more preferably gaseous $CO_2$, since it is possible to re-circulate non-used $CO_2/^{13}CO_2$.

If the reaction is carried out on a large scale (industrial scale) and/or if $^{13}CO_2$ is used, it is preferred to use one equivalent $CO_2$ per equivalent α-metalated vinyl ether in the method of the invention. Since it is preferred to directly use the crude reaction mixture from step a) in step b) one equivalent $CO_2$ per equivalent vinyl ether is used in step b), assuming a quantitative reaction in step a). For small scale laboratory reactions using an excess of $CO_2$ can be advantageous.

During the reaction of the step b), the reaction mixture is preferably heavily agitated, for instance stirred or vortexed, preferably stirred.

The crude α-alkoxy acrylic acid of formula (II) obtained in step b) may or may not be isolated before proceeding with step c). If the α-alkoxy acrylic acid of formula (II) obtained in step b) is not isolated, the method of the invention, i.e. steps a) to c) is carried out as a "one pot synthesis", which of course is less time consuming.

However, isolating the α-alkoxy acrylic acid of formula (II) obtained in step b) has shown to improve purity of pyruvic acid. Hence it is preferred to isolate the α-alkoxy acrylic acid of formula (II) obtained in step b) before proceeding with step c) of the method of the invention, if the synthesised pyruvic acid needs to be of high purity, e.g. if it is used to produce hyperpolarised $^{13}C$-pyruvate which is used as MR imaging agent.

The α-alkoxy acrylic acid of formula (II) obtained in step b) may be isolated by adding water and extraction with an organic solvent. Preferably non-polar solvents or polar aprotic solvents are used for extraction, more preferably dichloromethane, diethyl ether or THF and most preferably diethyl ether or dichloromethane. The aqueous and organic phases are separated and the aqueous phase is evaporated in vacuo to obtain α-alkoxy acrylic acid.

Since by using this procedure the isolated α-alkoxy acrylic acid still contains inorganic salts from the reaction with the alkyllithium base, it is preferred to precipitate these salts. Thus in a preferred embodiment, water is added first to quench the reaction, then an organic solvent is added for the extraction. The aqueous and organic phases are separated and the aqueous phase is evaporated in vacuo. The residue is re-dissolved in an aprotic non-polar solvent like acetonitrile or acetone, stirred, filtrated and the filtrate is subsequently evaporated to obtain α-alkoxy acrylic acid. In a more preferred embodiment, the obtained α-alkoxy acrylic acid is subsequently re-crystallized from a non-polar aprotic solvent like pentane or hexane.

In a more preferred embodiment α-alkoxy acrylic acid is isolated by the following procedure: water is added to quench the reaction after step b) and the organic solvents used in step a) are evaporated. The pH of the remaining aqueous phase is adjusted to about 2.5 to 3.5, most preferably to a pH of about 3 before the extraction with an organic solvent as described above. After extraction, the organic phase is preferably dried, e.g. over $MgSO_4$ and the organic solvent is evaporated. To improve purity of the isolated α-alkoxy acrylic acid, the compound can be re-crystallized from a non-polar aprotic solvent like pentane or hexane.

Purity of the α-alkoxy acrylic acid may be further enhanced by a 2-step extraction process, which is most preferred for isolating the α-alkoxy acrylic acid. As described above, water is added to quench the reaction after step b) and the organic solvents used in step a) are evaporated. The pH of the remaining aqueous phase is adjusted to about 7 and the aqueous phase is extracted with an organic solvent. After separating the phases, the pH of the aqueous phase is adjusted to about 2.5 to 3.5, more preferably to a pH of about 3 before a second extraction with an organic solvent. The organic phase is preferably dried, e.g. over $MgSO_4$ and the organic solvent is subsequently evaporated. To even further improve purity of the isolated α-alkoxy acrylic acid, the compound may be re-crystallized from a non-polar aprotic solvent like pentane or hexane.

In step c) of the method of the invention, the crude or isolated α-alkoxy acrylic acid of step b) is hydrolysed. Hydrolysis is readily achieved using a variety of mild acidic conditions, suitably diluted aqueous HCl, preferably 0.02-3 M aqueous HCl, in various kinds of solvents (for a review see R. W. Friesen, J. Chem. Soc., Perkin Trans. 1, 2001, 1969-2001). The presence of a solvent, especially a polar aprotic solvent like acetonitrile or acetone promotes the precipitation of salts which may be present in the reaction mixture if the α-alkoxy acrylic acid after step b) has not been isolated.

Hence, if the crude α-alkoxy acrylic acid is hydrolysed a polar aprotic solvent, preferably acetone or acetonitrile is used during hydrolysis. Residual salts from the alkyllithium base used in the method of the invention may be removed by an additional salt precipitation step, e.g. by adding a polar aprotic solvent and filtration of the precipitated salts.

Thus in one embodiment, a mixture of a polar aprotic solvent and aqueous HCl is added to the crude reaction mixture after step b). The mixture is evaporated to obtain pyruvic acid. In another preferred embodiment, the crude reaction mixture after step b) is quenched with water, evaporated to dryness and re-dissolved in aqueous HCl. The mixture is stirred for a while, again evaporated to dryness, re-dissolved in a polar aprotic solvent, preferably acetone or acetonitrile, filtered and the filtrate is evaporated to obtain pyruvic acid. In a most preferred embodiment, the crude reaction mixture after step b) is quenched with water and a polar aprotic is added. The mixture is stirred for a while and evaporated to dryness. The residue is re-dissolved in aqueous HCl and again a polar aprotic solvent is added. The mixture is filtrated and the filtrate is evaporated to obtain pyruvic acid.

If the isolated α-alkoxy acrylic acid is hydrolysed preferably no solvent is used and the diluted aqueous HCl is directly added to the isolated α-alkoxy acrylic acid. The reaction mixture is evaporated in vacuo to obtain pyruvic acid.

On a large scale (industrial scale), the method of the invention may be carried out as a batch synthesis. To avoid unnecessary use of $CO_2/^{13}CO_2$ the method of the invention may be carried out in a closed batch reactor similar to a hydrogenation reactor so that one equivalent of $CO_2/^{13}CO_2$ is used and the gas consumption can be monitored.

Further the method of the invention may be carried out in a micro reactor system comprising of a reaction chamber for the reaction of step a), i.e. the synthesis of the α-metalated vinyl ether and a container for $CO_2/^{13}CO_2$. Both compounds, i.e. $CO_2/^{13}CO_2$ and the α-metalated vinyl ether are then combined in a reaction vessel and the product is collected in a collection chamber.

In another embodiment of the method of the invention can be carried out on a solid inert support. Thus the vinyl ether of formula (I) or alternatively the α-metalated vinyl ether may be adsorbed to a suitable solid support and the material may for instance be filled in a column. Alternatively, a micro reactor may be used and the solid support with the absorbed vinyl ether or α-metalated vinyl ether is immobilised inside a column in said micro reactor. The column is preferably flushed with an inert gas like argon or nitrogen before the reaction with the alkyllithium base and/or $CO_2/^{13}CO_2$. With this method, any excess $CO_2/^{13}CO_2$ may be recovered downstream and re-used.

The invention is further illustrated by way of the following non-limiting examples.

EXAMPLES

Example 1

One Pot Synthesis of Pyruvic Acid Using Tert-BuLi as Alkyllithium Base and Ethyl Vinyl Ether as a Starting Material a) Under $N_2$-atmosphere a mixture of THF-THP (50 ml, 1:1) was cooled to −78° C. and ethyl vinyl ether was added drop wise (1.082 ml, 11.3 mmol). Tert-BuLi (8.82 ml, 1.7 M in pentane) was added drop wise to the resulting mixture and the mixture was allowed to warm up to −5-0° C.

b) An atmospheric pressure of $CO_2$ was then subjected to the reaction mixture under vigorous stirring for 20 min.

c) To the stirred mixture was then added a 3:1 mixture of acetone and aqueous HCl (3 M, 24 ml) and the resulting mixture was brought to ambient temperature over a period of 1 h. The reaction mixture was then evaporated in vacuo. NMR of the crude product indicated formation of the desired product, however in relatively low quantity.

Example 2

One Pot Synthesis of Pyruvic Acid Using Lochmann-Schlosser Base and Ethyl Vinyl Ether as a Starting Material a) To THF (30 ml) was added ethyl vinyl ether (1.92 ml, 20 mmol), tert-BuOK (2.24 g, 20 mmol) and TMEDA (3.0 ml, 20 mmol) under $N_2$-atmosphere. The resulting mixture was cooled to −78° C. before n-BuLi (12.05 ml, 20 mmol, 1.66 M dissolved in hexane) was added drop wise over a period of 10 min. The reaction mixture was stirred at this temperature for another 30 min.

b) An atmospheric pressure of $CO_2$ was then subjected to the reaction mixture under vigorous stirring (vortexing) for 5 min. The cooling bath was then removed and the reaction mixture was allowed to slowly warm up to ambient temperature. The reaction mixture was stirred at ambient temperature for 5 min and quenched by addition of $H_2O$ (10 ml).

c) The crude product was evaporated in vacuo to dryness before it was re-dissolved in aqueous HCl (50 ml, 2 M) and stirred at ambient temperature for 3 h. The water was evaporated in vacuo and acetone (50 ml) was added to the residue. The resulting mixture was stirred at 40° C. for a period of 15 min, then the mixture was filtered and the filtrate was evaporated in vacuo. According to IR and MS, pyruvic acid was obtained, however in relatively low purity yield. The product contained inorganic salts.

Example 3

One Pot Synthesis of Pyruvic Acid Using Lochmann-Schlosser Base and Ethyl Vinyl Ether as a Starting Material a) To THF (50 ml) was added ethyl vinyl ether (4.79 ml, 50 mmol), tert-BuOK (5.61 g, 50 mmol) and TMEDA (7.51 ml, 50 mmol) under $N_2$-atmosphere and the resulting mixture was cooled to −78° C. before n-BuLi (30.12 ml, 50 mmol, 1,66 M in hexane) was added drop wise over a period of 10 min. The reaction mixture was stirred at this temperature for 30 min.

b) An atmospheric pressure of $CO_2$ was then subjected to the reaction mixture under vigorous stirring (vortexing) for 5 min. The cooling bath was then removed and the reaction mixture was allowed to slowly warm up to ambient temperature. The reaction mixture stirred at this temperature for 5 min and quenched by addition of $H_2O$ (50 ml).

c) Acetone (150 ml) was added and the mixture was stirred for 10 min, then filtered and evaporated in vacuo. The residue was re-dissolved in aqueous HCl (50 ml, 2 M) and stirred at ambient temperature for 3 h. Acetonitrile (50 ml) was added and the mixture was filtered and evaporated in vacuo. Pyruvic acid was obtained as a yellow oil, yield 2.13 g (48%), purity (57%) both determined by NMR.

Example 4

One Pot Synthesis of Pyruvic Acid Using the Lochmann-Schlosser Base and Ethyl Vinyl Ether as a Starting Material a) To THF (50 ml) was added ethyl vinyl ether (4.79 ml, 50 mmol), tert-BuOK (5.61 g, 50 mmol) and TMEDA (7.51 ml, 50 mmol) under $N_2$-atmosphere and the resulting mixture was cooled to −78° C. before n-BuLi (30.12 ml, 50 mmol, 1.66 M in hexane) was added drop wise over a period of 10 min. The reaction mixture was stirred at this temperature for 30 min.

b) An atmospheric pressure of $CO_2$ was then subjected to the reaction mixture under vigorous stirring (vortexing) for 5 min. The cooling bath was then removed and the reaction mixture was allowed to slowly warm up to ambient temperature. The reaction mixture was stirred at this temperature for 5 min and quenched by addition of $H_2O$ (40 ml).

c) The residue was extracted with diethyl ether (3 times with 50 ml each) before the aqueous phase was evaporated in vacuo to give an oily liquid. The oily liquid was re-dissolved in water and acetonitrile (150 ml) was added. The precipitate formed was filtered off and the organic phase was evaporated in vacuo. The residue was re-dissolved in aqueous HCl (50 ml, 2 M) and stirred at ambient temperature for 3 h. The process described for salt precipitation was repeated 2 times with 50 ml acetonitrile. After final evaporation pyruvic acid was obtained as a yellow oil, yield 1.17 g (36%) purity (57%) both determined by NMR. The product contained inorganic salts.

Example 5

Synthesis of Pyruvic Acid Using Lochmann-Schlosser Base and Ethyl Vinyl Ether as a Starting Material and Isolation of α-Ethoxy Acrylic Acid After Step b)

a) To THF (100 ml) was added ethyl vinyl ether (4.79 ml, 50 mmol), tert-BuOK (5.61 g, 50 mmol) and TMEDA (7.51 ml, 50 mmol) under $N_2$-atmosphere and the resulting mixture was cooled to −78° C. before n-BuLi (20.41 ml, 50 mmol, 2.45 M in hexane) was added drop wise over a period of 10 min and stirred at this temperature for 30 min.

b) An atmospheric pressure of $CO_2$ was then subjected to the reaction mixture under vigorous stirring (vortexing) for 5 min. The cooling bath was then removed and the reaction mixture was allowed to slowly warm up to ambient temperature. The reaction mixture was stirred at this temperature for 5 min and quenched by addition of $H_2O$ (50 ml). The reaction mixture was extracted with diethyl ether (3 times, each 50 ml), and the organic and water phase were separated. The aqueous phase was evaporated in vacuo and acetonitrile (150 ml) was added. The resulting mixture was stirred for 15 min at ambient temperature, filtered and the filtrate was evaporated in vacuo.

The α-ethoxy acrylic acid obtained contained inorganic salts (approximately 15% in total as determinated by ICP).

c) The α-ethoxy acrylic acid from step b) was dissolved in aqueous HCl (2 M) and stirred at room temperature for about 4 hours. The reaction mixture was evaporated in vacuo and pyruvic acid was obtained as viscous oil.

Example 6

Synthesis of Pyruvic Acid Using Lochmann-Schlosser Base and Ethyl Vinyl Ether as a Starting Material and Isolation of α-Ethoxy Acrylic Acid After Step b)

a) To THF (160 ml) was added ethyl vinyl ether (7.66 ml, 80 mmol), tert-BuOK (8.98 g, 80 mmol) and TMEDA (12.01 ml, 80 mmol) under $N_2$-atmosphere. The resulting mixture was cooled to −78° C. before n-BuLi (32.65 ml, 80 mmol, 2.45 M in hexane) was added drop wise over a period of 10-15 min and stirred at this temperature for 30 min.

b) An atmospheric pressure of $CO_2$ was then subjected to the reaction mixture under vigorous stirring for 5 min. The cooling bath was then removed and the reaction mixture was allowed to slowly warm up to ambient temperature. The reaction mixture was stirred at this temperature for 5 min and quenched by addition of $H_2O$ (80 ml).

THF was evaporated under reduced pressure at 30° C. and the pH of the aqueous residual phase was adjusted to about 7. Aqueous saturated NaCl (60 ml) was added and the mixture was extracted with diethyl ether (3 times, 100 ml each). The combined diethyl ether phases were dried over $MgSO_4$, filtered and evaporated in vacuo. HPLC of the residue indicated no presence of the desired product. The pH in the residual aqueous phase was then adjusted to about 3 and the mixture was extracted with diethyl ether (3 times, 100 ml each). The combined diethyl ether phases were dried over $MgSO_4$, filtered and evaporated in vacuo. The desired product α-ethoxy acrylic acid was obtained as light yellow powder which was re-crystallized from pentane/dichloromethane (40 ml/4 ml). Yield 25%; purity higher than 95% as determined by HPLC and NMR c) The α-ethoxy acrylic acid from step b) was dissolved in aqueous HCl (2 M) and stirred at room temperature for about 4 hours. The reaction mixture was evaporated in vacuo and pyruvic acid was obtained as viscous oil.

Example 7

Synthesis of Pyruvic Acid Using Lochmann-Schlosser Base and Ethyl Vinyl Ether as a Starting Material and Isolation of α-Ethoxy Acrylic Acid After Step b)

a) To THF (30 ml) was added ethyl vinyl ether (1.0 ml, 10.5 mmol), tert-BuOK (1.18 g, 10.5 mmol) and TMEDA (1.22 g, 10.5 mmol) under $N_2$-atmosphere. The mixture was cooled to −78° C. before n-BuLi (1.6 M in hexane, 6.6 ml) was added over a period of 10 min and the reaction mixture was stirred for 30 min.

b) The reaction was then subjected to an atmospheric pressure of $CO_2$ under heavy stirring (vortexing) for 30 min. The reaction mixture was allowed to slowly warm up to ambient temperature. The reaction mixture was added water (20 ml) and THF was removed in vacuo at 30° C.

The pH of the remaining aqueous phase was adjusted to 2.5-3 by addition of aqueous HCl (3 M) before being extracted with diethyl ether (3 time 50 ml each). The combined diethyl ether phases were dried over $MgSO_4$, filtered and evaporated in vacuo at 30° C. The residue was re-crystallized from hexane to give the product α-ethoxy acrylic acid as white crystalline needles. Yield: 350 mg (29%), purity 91%, both determined by NMR.

c) α-ethoxy acrylic acid from step b) (0.58 g, 5 mmol) was dissolved in aqueous HCl (2 M, 5.5 ml) and stirred at room temperature for 4 h. The reaction mixture was evaporated in vacuo and pyruvic acid was obtained as viscous oil. Yield: 430 mg (99%). Purity: 99.3%, both determined by NMR.

SPECIFIC EMBODIMENTS, CITATION OF REFERENCES

The present invention is not to be limited in scope by specific embodiments described herein. Indeed, various modifications of the inventions in addition to those described herein will become apparent to these skilled in the art from the foregoing description. Such modifications are intended to fall within the scope of the appended claims.

Various publications and patent applications are cited herein, the disclosures of which are incorporated by reference in their entireties.

What is claimed is:

1. Method for producing pyruvic acid by
   a) reacting a vinyl ether of formula (I)

(I)

wherein
R is a straight chain or branched $C_1$-$C_6$-alkyl group or an aliphatic or aromatic ring comprised of 5-7 carbon atoms, optionally substituted with one or more lower alkyl groups, halogen groups or nitro groups with an alkyllithium base to obtain an α-metalated vinyl ether b) reacting the α-metalated vinyl ether obtained in step a) with $CO_2$ to obtain an α-alkoxy acrylic acid of formula (II)

wherein
R is defined as above; and c) subsequently hydrolysing the α-alkoxy acrylic acid of formula (II).

2. Method according to claim 1 wherein R is ethyl, n-propyl, isopropyl, n-butyl, isobutyl or tert-butyl.

3. Method according to claim 1 wherein the alkyllithium base is a butyllithium (BuLi) base.

4. Method according to claim 1 wherein in step a) one or more additives that increase the reactivity of the alkyllithium base are added.

5. Method according to claim 4 wherein the additive is tert-BuOK.

6. Method according to claim 1 wherein gaseous or super-critical $CO_2$ is used in step b).

7. Method according to claim 1 wherein steps a) to c) are carried out in a one pot synthesis.

8. Method according to claim 1 wherein the α-alkoxy acrylic acid of formula (II) obtained in step b) is isolated before proceeding with step c).

9. Method according to claim 8 wherein the α-alkoxy acrylic acid of formula (II) is isolated by addition of water and extraction with an organic solvent.

10. Method according to claim 9 wherein after said addition of water the pH of water phase obtained is adjusted to about 2.5 to 3.5.

11. Method according to claim 8 wherein in a subsequent step the isolated α-alkoxy acrylic acid of formula (II) is re-crystallized from a non-polar aprotic solvent.

12. Method according to claim 1 wherein the hydrolysis in step c) is carried out with diluted aqueous HCl.

13. Method according to claim 1 wherein said method is used for producing $^{13}C_1$-pyruvic acid or $^{11}C_1$-pyruvic acid by using $^{13}CO_2$ or $^{11}CO_2$ in step b).

14. The method of claim 1 wherein R is ethyl.

15. The method of claim 1 wherein the alkyllithium base is n-BuLi, sec-BuLi or tert-BuLi.

* * * * *